United States Patent [19]

Harris

[11] 4,091,033
[45] May 23, 1978

[54] METHOD OF MAKING 2-ALKOXY-2,3-DIHYDRO-BENZOFURAN-5-OLS AND THEIR ALKYL SULFONIC ACID ESTERS

[75] Inventor: John Frederick Harris, Meldreth Nr. Royston, England

[73] Assignee: Fisons Limited, London, England

[21] Appl. No.: 812,623

[22] Filed: Jul. 5, 1977

Related U.S. Application Data

[63] Continuation-in-part of Ser. No. 605,627, Aug. 18, 1975, abandoned.

[30] Foreign Application Priority Data
Sep. 5, 1974 United Kingdom ............... 38814/74
Sep. 5, 1974 United Kingdom ............... 38815/74
Sep. 5, 1974 United Kingdom ............... 38818/74

[51] Int. Cl.$^2$ .......................................... C07D 307/83
[52] U.S. Cl. ........................ 260/346.22; 260/346.71; 260/346.73
[58] Field of Search ............... 260/346.2 R, 293.58, 260/247.15, 346.71

[56] References Cited

U.S. PATENT DOCUMENTS 3,412,109 11/1968 Skaletsky ................... 260/346.22
3,689,507 9/1972 Gates et al. ................ 260/346.22

Primary Examiner—Henry R. Jiles
Assistant Examiner—Bernard Dentz
Attorney, Agent, or Firm—Wenderoth, Lind & Ponack

[57] ABSTRACT

Compounds of the formula:

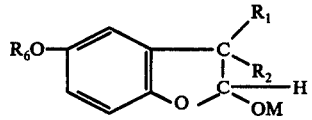

wherein $R_1$ and $R_2$ are the same or different and each is selected from the group consisting of hydrogen, an alkyl group and together, an alkylene chain; M is alkyl of 1 to 6 carbon atoms; and $R_6$ is selected from the group consisting of hydrogen and $R_5SO_2$— wherein $R_5$ is alkyl of 1 to 6 carbon atoms, are prepared by a procedure in which the key step is reacting benzoquinone with an enamine $R_1R_2C=CHNR_3R_4$ in the presence of a compound of the formula $R_1R_2CHCHO$. The product contains a lower proportion of hydroquinone impurity and is useful as a herbicide.

9 Claims, No Drawings

METHOD OF MAKING 2-ALKOXY-2,3-DIHYDRO-BENZOFURAN-5-OLS AND THEIR ALKYL SULFONIC ACID ESTERS

The present invention relates to a process for the preparation of a chemical compound, and is a continuation-in-part. Application of our parent Application No. 605,627, filed Aug. 18, 1975 and now abandoned.

Compounds of the general formula:

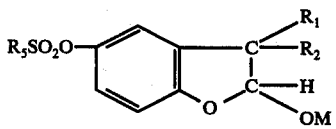

I

[wherein $R_1$ and $R_2$ may be the same or different and each is selected from hydrogen or an alkyl group (notably a lower alkyl group, the term lower is used herein to denote a group containing from 1 to 6 carbon atoms, for example a methyl, an ethyl or a propyl group) or $R_1$ and $R_2$ together form an alkylene chain (e.g. one containing from 2 to 5 carbon atoms) and M is a lower alkyl group and $R_5$ is an alkyl group (notably a lower alkyl group, for example a methyl, ethyl or propyl group)] find use as herbicides. However, solutions prepared from the compounds of formula I are unsatisfactory in that they develop precipitates on standing. We have found that these precipitates are caused by the presence of hydroquinone derived materials and that, surprisingly, if intermediate compounds containing less than 1 molar percent of hydroquinone based impurities, i.e. impurities of the formula

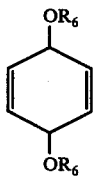

where $R_6$ is hydrogen or a group $R_5SO_2$—, are converted to the compounds of formula I little or no further quantities of hydroquinone based materials are formed and that it is possible to produce compounds of formula I which are contaminated with less than 1 molar percent of hydroquinone derived impurities. It is thus possible to produce herbicidal solutions with a reduced tendancy to form precipitates.

Accordingly, from one aspect the present invention provides a process for preparing a compound of formula

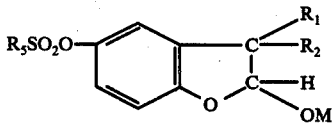

I

[wherein $R_1$ and $R_2$ may be the same or different and each is selected from hydrogen or an alkyl group or $R_1$ and $R_2$ together form an alkylene chain; M is a lower alkyl group containing from 1 to 6 carbon atoms; and $R_5$ is an alkyl group] characterised in that a compound of formula:

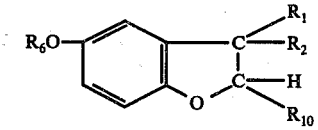

II

[wherein $R_{10}$ is a group OM or a group —$NR_3R_4$ and $R_6$ is hydrogen or is $R_5SO_2$— when $R_{10}$ is —$NR_3R_4$; $R_3$ and $R_4$ may be the same or different and each is selected from a lower alkyl group or together with the N atom form a heterocyclic ring; and $R_1$, $R_2$, and $R_5$ have the values given above] which is contaminated with less than 1 molar percent of hydroquinone based materials is reacted to convert the —OH group into an $R_5SO_2O$— group and/or to convert the —$NR_3R_4$ group into an —OM group whereby there is produced a compound of formula I.

The invention also provides a compound of formula I or a compound of formula II and herbicidally active derivatives of the compound of formula I characterised in that the compounds contain less than 1 molar percent thereof of hydroquinone derived impurities.

The hydroquinone derived impurities in the compounds are readily detected by gas/liquid chromatography. It is preferred that the impurities be present in less than 0.5 molar percent.

The compound of formula II may be converted directly or indirectly to the compound of formula I, but the conversion is conveniently done by reacting the compound of formula II with a compound of formula $R_5SO_2Hal$ (where Hal is halogen — notably chlorine) to convert the 5—OH group into a —$OSO_2R_5$ group; and/or converting the 2—$NR_3R_4$ group into an —OM group by hydrolysis and alkoxylation. These conversions may be carried out in either order.

The conversion of the —$NR_3R_4$ group in the compound of formula II is hydrolysed and alkoxylated by treatment with an acid and an alkanol. Preferably the conversion is carried out in a single stage by using a mixture of acid and alkanol.

The acid used is a strong acid, which may be a mineral acid or an organic acid; which does not take part in deleterious side reactions during the conversion, apart from forming a salt with the amine $HNR_3R_4$ released during the process; and which preferably dissociates in water to give at least 1 gram equivalent of $H^+$ per gram mol of acid. Thus, suitable acids for present use include hydrochloric, sulphuric and phosphoric acids, but do not include nitric acid which may oxidise the reagents and/or products. The acid may be used in the form of an aqueous solution thereof or in an anhydrous form. The mineral acid for present use is preferably hydrochloric acid which desirably provides not less than 20 parts by weight of HCl per 80 parts of water in the reaction mixture.

The compound HOM is, as indicated in the preferred compounds which it is desired to produce, preferably a lower alkanol, notably methanol, ethanol, propanol or iso-propanol.

The conversion of the —$NR_3R_4$ group is preferably carried out in a liquid medium, which may be merely an excess of the alkanol reagent. However, the process is conveniently carried out by adding the solution of the compound of formula II produced in an earlier preparative stage as outlined below to an agitated mixture of the acid and alkanol so as to form a two phase reaction mixture. The addition may take place in one or more stages or may be on a continuous basis where the process is operated continuously. The reaction may be carried out at elevated temperatures, although it is preferred to use temperatures below 40° C.

We have found that the relative proportions of acid, alkanol, and compound of formula II affect the yield and quality of the product. We prefer to employ more than 1.5 molar proportions of alkanol and more than 1.2 molar equivalent proportions of acid per molar proportion of compound of formula II. Whilst the process may be carried out under substantially anhydrous conditions, as when $H_2SO_4$ is used as the acid, water may be preferred with some acids, e.g. when HCl is present. In this case we prefer to use more than 0.35 parts by weight of HCl per part of water in the reaction mixture.

It is preferred to agitate the reaction mixture and it will be appreciated that all weights and proportions are in respect of the total reaction mixture not just the organic or aqueous phase.

Apart from the reagents and solvents, the reaction mixture may contain minor amounts of other non-deleterious materials. Thus, the compound of formula II need not be in pure form but may be used in the form of the reaction product from an earlier process step as outlined below.

The product, which is a compound of formula I or a compound of formula II having the group $R_{10}$ as —OM may be recovered from the reaction mixture by allowing the mixture to separate into organic and aqueous phases, removing the organic layer and recovering the product therefrom, e.g. by distillation (to remove excess alkanol and solvent when present), washing with a mild alkali (e.g. sodium carbonate) and further distillation, preferably under reduced pressure, to remove final amounts of solvent. The isolated product may then be purified by conventional techniques.

As indicated by formula II, the product of the process of the above conversion may have the 5-position in the form of a 5-OH group or a derivative thereof, or a group —$OSO_2R_5$. However, it is preferred that the 5-position be in the form of an $R_5SO_2O$— group. This group is preferably a $CH_3SO_2O$— group and is preferably introduced into the intermediate compound of formula II by reacting this compound with $HalSO_2R_5$ in the presence of an acid acceptor (Hal being halogen, notably chlorine) before the conversion of the $NR_3R_4$ has been carried out as described above.

In reacting a compound of formula II with Hal SO$_2$R$_5$, the reaction is carried out in the presence of an acid acceptor which includes tertiary amines, notably trialkylamines, e.g. trimethylamine or triethylamine; tertiary aromatic amies, e.g. dimethyl-aniline; and pyridine and its homologues. Whilst the reagents may be used in substantially the stoichiometric amounts, we prefer to use a small excess, e.g. up to 20% molar excess, of the compound R$_5$SO$_2$Hal based on the compound of formula II and an excess, e.g. 10 to 50% molar excess, of acid acceptor based on the amount of H-Hal which would theoretically be liberated.

The reaction may be carried out merely by mixing together the R$_5$SO$_2$Hal and compound of formula II simultaneously or sequentially and in one or more stages. Desirably the reaction temperature is less than 100° C, preferably within the range 30° to 80° C. However, to aid uniform reaction we prefer to carry out the reaction in an organic solvent as reaction medium, or in an excess of the acid acceptor. Suitable solvents include non-polar organic solvents, e.g. benzene, toluene, xylene or hexane.

When the reaction is substantially complete, as evidenced by analysis of a sample showing little or no remaining initial compound of formula II having R$_6$ as hydrogen, the product may be recovered using conventional techniques. However, where the compound of formula II has not been subjected to conversion of the NR$_3$R$_4$ group, we prefer not to isolate the product but merely to extract the halogen salt of the acid acceptor from the reaction mixture by water extraction and separate off the organic layer containing the compound of formula II for treatment with an acid and alkanol as described above.

The compounds of formula II containing less than 1 molar percent of hydroquinone based impurities may be obtained, for example, by distilling or otherwise purifying crude compounds to remove the impurities. However, we have surprisingly found that the compounds of formula II having R$_6$ as hydrogen and R$_{10}$ as —NR$_3$R$_4$ of sufficient purity for present use may be produced by the reaction of benzoquinone with a compound of the formula:

$$R_1R_2C\!=\!CH\!-\!NR_3R_4 \qquad \text{III}$$

the reaction being carried out in the presence of a compound of the formula $R_1R_2CHCHO$.

From another aspect, the present invention provides a process for preparing a compound of formula II or a derivative thereof which comprises reacting benzoquinone with a compound of formula III characterised in that the reaction is carried out in the presence of a compound of formula $R_1R_2CHCHO$ wherein $R_1$ and $R_2$ have the values given above.

This process for preparing the compounds of formula II is of especial use in the preparation of compounds of formula II in which $R_1$ and $R_2$ are the same lower alkyl (notably methyl or ethyl) and the group —NR$_3$R$_4$ is selected from piperidino, morpholino, and pyrrolidino. In this case the compound of formula R$_1$R$_2$CHCHO will be an aliphatic aldehyde, notably isobutyraldehyde.

The above process for preparing the compounds of formula II will usually be carried out in the presence of a liquid medium. Suitable liquid media for present use include aromatic hydrocarbons, e.g. benzene, toluene or xylene; aliphatic hydrocarbons, e.g. cyclohexane or petroleum ethers; halogenated hydrocarbons; and aliphatic ketones, e.g. acetone and methyl ethyl ketone. If desired the liquid medium may be provided wholly or in part by the compound R$_1$R$_2$CHCHO, e.g. when isobutyraldehyde is used. However, it is preferred to use a liquid medium in which the compound of formula II and water are only slightly soluble or miscible. Exemplary of such liquid media are the aromatic hydrocarbons.

The benzoquinone and compound of formula III are conveniently used in the forms of solutions or slurries in one of the liquid media specified above and the reaction is preferably carried out with agitation and at a temperature of from 20° to 60° C, e.g. 40 to 50° C, although lower or higher temperatures, e.g. up to the reflux temperature of the reaction mixture, may be used. Where the reaction is not carried out under reflux, it may be desirable to heat the reaction mixture, e.g. to 100°–120° C, in the final stages to assist completion of the reaction.

The amount of the compound of formula R$_1$R$_2$CHCHO which is present is preferably at least 10, e.g. 10 to 200, molar percent, based on the amount of the compound of formula III and is typically in the range 20 to 100 molar percent. The presence of the compound R₁R₂CHCHO may be achieved by separate addition of the compound to the reaction mixture or by the use of the compound as a solvent or carrier for either or both of the other reagents. However, a convenient method for incorporating the compound R₁R₂CHCHO is to use the reaction mixture in which the compound of formula III is prepared. Thus, the compound of formula III may be prepared by reacting a compound H—NR₃R₄ with an excess, e.g. 10 to 200%, notably 20–100%, molar excess, of the compound R₁R₂CHCHO and the reaction product used directly in the preparation of the compounds of formula II without purification, although it will usually be necessary to remove water therefrom, e.g. by distillation. The present invention therefore also provides a process for preparing a compound of formula II or a derivative thereof which comprises reacting a compound of formula H—NR₃R₄ with an excess of a compound of formula R₁R₂CHCHO to give a reaction mixture containing a compound of formula III and the compound R₁R₂CHCHO; and reacting this reaction mixture with benzoquinone.

Whilst the above preparation of the compound of formula II may be carried out by adding a solution of the enamine of formula III to a solution or slurry of the benzoquinone, we have found that the product of such a reaction may be discoloured due to side reactions and surprisingly that these side reactions are suppressed if the enamine is present for most or all of the reaction period in more than the stoichiometric amount required to react with the benzoquinone.

The presence of the requisite amount of enamine in the reaction mixture can be achieved by, for example, adding the benzoquinone either as a single addition or progressively over a period of time to a reaction mixture containing the desired amount of enamine; or by adding the benzoquinone and enamine in the desired proportions to a continuously operated process. Preferably, the overall excess of the enamine employed is from 1 to 10%, notably 1 to 4%, molar although higher excess may be used if desired and during the initial stages of a batch process where benzoquinone is added progressively to the enamine much larger excesses may occur.

Thus, the present invention also provides a process for preparing a compound of formula II or a derivative thereof which comprises reacting a compound of formula H—NR₃R₄ with an excess of a compound of formula R₁R₂CHCHO in the presence of an organic solvent to form a reaction mixture containing a compound of formula III; and reacting this reaction mixture with benzoquinone, the compound of formula III being present in the reaction mixture at substantially all times in more than the stoichiometric amount required to react with the benzoquinone present in the reaction mixture. The invention also comprises a process for preparing a compound of formula II or a derivative thereof which process comprises reacting benzoquinone with a compound of formula III characterised in that the reaction is carried out in the presence of a compound of formula R₁R₂CHCHO and in that at substantially all times during the reaction the compound of formula III is present in more than the stoichiometric amount required to react with the benzoquinone present in the reaction mixture.

The above processes for preparing the compounds of formula II may be carried out batchwise or as a continuous process and the product of formula II may be recovered using customary techniques, e.g. by filtering the reaction mixture in which it is produced to recover the solid product which may thereafter be washed. However, where the compound of formula II is to be used directly in the production of the compounds of formula I, it may not be necessary to separate it from the reaction mixture.

The present invention therefore also provides a process for preparing a compound of formula

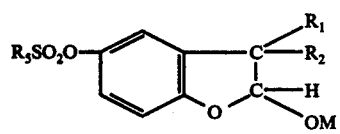

I

[wherein R₁ and R₂ may be the same or different and each is selected from an alkyl group and M and R₅ may be the same or different and each is an alkyl group] which comprises reacting benzoquinone with an enamine of formula:

III

[wherein R₁ and R₂ have the values given above and R₃ and R₄ may be the same or different and each is selected from a lower alkyl group or R₃ and R₄ together with the N atom form a heterocyclic ring] in the presence of a compound of formula R₁R₂CHCHO, the enamine preferably being present at substantially all times during the reaction period in more than the stoichiometric amount required to react with the benzoquinone; whereby there is produced a compound of formula

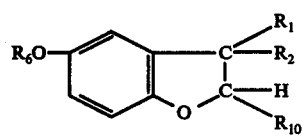

II wherein R₆ is hydrogen and R₁₀ is —NR₃R₄; and converting the R₆ group to a group —OSO₂R₅ converting the group R₁₀, either before or after the conversion of the R₆ group, to a group —OM (wherein M and R₅ have the values given above).

The above process stages may be carried out as distinct and separate steps but, as indicated above, readily lend themselves to sequential operation in a later stage. Furthermore, it is possible to recover excess reagents and solvents for re-use. Thus, acid acceptor may be recovered from the aqueous phase from conversion of the R₆ group by treatment of the halogen salt with alkali (e.g. NaOH) and subsequent distillation; the organic phase of the reaction mixtures from the conversion of the R₁₀ group may be fractionally distilled to recover alkanol and solvent; and the aqueous phases from the conversion of the R₁₀ group may be distilled to recover alkanol and, possibly, acid, the residue than being treated with alkali to liberate the amine HNR₃R₄ and any acid acceptor which may have been carried over in the organic phase from the prior conversion of the R₆ group and this residue is then fractionally distilled to recover amine for use in the preparation of the compound and to recover acid acceptor for use in the conversion of the R₆ group.

The process of the invention will now be illustrated by the following Examples, in which all parts and percentages are given by weight unless stated otherwise:

EXAMPLE 1

Preparation of enamine

To a stirred mixture of 332 parts of isobutyraldehyde (100% molar percent excess) with 867.5 parts of toluene were added 200.5 parts of morpholine. The temperature rose from 20° to 41° C. The mixture was refluxed with continuous separation and removal of the aqueous phase from the returning solvent stream. To complete the water removal, the final stages were carried out with a fractionation column. The total time at reflux was 4.8 hours.

Preparation of 2,3-dihydro-3,3-dimethyl-5-hydroxy-2-morpholinobenzofuran

To 54 parts of technical benzoquinone were added 51.5 parts of toluene and to this slurry was added sufficient of the enamine solution as prepared above to be equal to a 4% molar excess of enamine to technical benzoquinone. The time of addition was 0.7 hours, reaction temperature 40°–45° C during addition. After a further 0.7 hours the reaction mixture was raised to the boiling point and maintained at reflux for 0.25 hours. After cooling to 25° C the insoluble product was filtered off, washed with toluene, and air dried to constant weight giving 2,3-dihydro-3,3-dimethyl-5-hydroxy-2-morpholinobenzofuran.

The yield of 2,3-dihydro-3,3-dimethyl-5-hydroxy-2-morpholino-benzofuran was 89.3% based on the benzoquinone starting material and the purity was 98.7% by analysis. The hydroquinone impurity in the product was 0.2%.

Comparative example

The above steps were repeated, except that the enamine solution was fractionally distilled to remove untreated isobutyraldehyde so that no significant amount of isobutyraldehyde should be present during reaction of the enamine with the benzoquinone. In this case the 2,3-dihydro-3,3-dimethyl-5-hydroxy-2-morpholino-benzofuran was produced in 89.2% yield and at a purity of 96.1%. The hydroquinone content was 1.6%.

EXAMPLE 2

The process of the Comparative Example was repeated, except that isobutyraldehyde in an equimolar amount based in the enamine used, was added as a separate feed to the reaction vessel in which the 2,3-dihydro-3,3-dimethyl-5-hydroxy-2-morpholinobenzofuran was being prepared. The product was produced in 90% yield, at a purity of 97.8% and with a hydroquinone content of 0.2%.

EXAMPLE 3

To a stirred mixture of 332 parts of isobutyraldehyde (100% molar percent excess) with 867.5 parts of toluene were added 200.5 parts of morpholine. The temperature rose from 20° to 41° C. The mixture was refluxed with continuous separation and removal of the aqueous phase from the returning solvent stream. To complete the water removal, the final stages were carried out with a fractionation column. The total time at reflux was 4.8 hours. To this enamine solution was added a total of 238.2 parts of technical benzoquinone (95.7% molar on the morpholine assuming 100% conversion to enamine) over a period of 1.2 hours. The temperature was maintained at 35°–45° C throughout the addition by heating or cooling as required. When the heat of reaction was no longer observed, the reaction mixture was raised to the boiling point and maintained at reflux for 0.5 hours. After cooling to 25° C the insoluble product was filtered off, washed with 670 parts of toluene, and air dried to constant weight giving 505.1 parts of 2,3-dihydro-3,3-dimethyl-5-hydroxy-2-morpholino-benzofuran, yield 91.7% based on the technical benzoquinone used.

EXAMPLE 4

To a slurry of 10% parts of benzoquinone in 104 parts of toluene was added 0.52 molar equivalents of enamine dissolved in toluene and isobutyraldehyde and prepared in a similar manner to the enamine solution used in Example 3. The addition time was 0.75 hours, reaction temperature 40°–45° C. The reaction mixture was left agitating for 16 hours before a further 0.52 molar equivalents of enamine solution was added. After refluxing the reaction mixture and isolating the product as described in Example 1, 208.3 parts were obtained, equivalent to an 83.6% yield based on the technical benzoquinone used.

Whereas the product obtained in Example 3 was light tan in colour, the product from this Example was grey.

EXAMPLE 5

Preparation of 2,3-dihydro-3,3-dimethyl-2-morpholino-benzofuran-5-yl methane sulphonate The product from Example 1 (112.5 parts) was reslurried in 350 parts of toluene and heated to 40° C with agitation. Methane sulphonyl chloride (56.5 parts) and triethylamine (50.5 parts) were added simultaneously but separately to the reaction mixture, which was maintained at 40°–46° C, over a period of 0.35 hours. A further 5 parts of triethylamine were added, followed by 110 parts of water. The two phase reaction mixture was heated to 50°–55° C and then allowed to separate. The lower, triethylamine hydrochloride, layer was removed. The upper organic layer was evaporated to dryness to give solid 2,3-dihydro-3,3-dimethyl-2-morpholino-benzofuran-5-yl methane sulphonate. Preparation of 2,3-dihydroxy-benzofuran-5-yl-methane sulphonate crystals. The crystals were dissolved in ethanol containing 2 drops of sulphuric acid and refluxed for one hour. The mixture was then cooled, neutralised with triethylamine and evaporated to about one quarter of its volume. Water was added to precipitate 2,3-dihydro-3,3-dimethyl-2-ethoxy-benzofuran-5-ylmethane sulphonate. This product contained 0.4% dimesylquinol impurity as compared to 2% in a product produced from material derived from the Comparative Example to Example 1.

EXAMPLE 6

Stage (a)

To a stirred mixture of 332 parts of isobutyraldehyde (100% molar percent excess) with 867.5 parts of toluene were added 200.5 parts of morpholine. The temperature rose from 20° to 41° C. The mixture was refluxed with continuous separation and removal of the aqueous phase from the returning solvent stream. To complete the water removal, the final stages were carried out with a fractionation column. The total time at reflux was 4.8 hours.

To the enamine solution thus produced was added a total of 238.2 parts of technical benzoquinone over a period of 1.2 hours. The temperature was maintained at 35°–45° C throughout by heating or cooling as required. When the heat of reaction was no longer observed, the reaction mixture was raised to the boiling point and maintained at reflux for 0.5 hours. After cooling to 25° C the insoluble product was filtered off, washed with 670 parts of toluene, and air dried to constant weight giving 505.1 gms of 2,3-dihydro-3,3-dimethyl-5-hydroxy-2-morpholinobenzofuran. Yield 91.7% on the technical benzoquinone used.

Stage (b)

The product from Stage (a) (505.1 parts) was reslurried in 1083 parts of toluene and heated to 40° C with agitation. Methane sulphonyl chloride (258 parts) and triethylamine (228 parts) were added simultaneously but separately to the reaction mixture, which was maintained at 40°–46° C, over a period of 0.35 hours. A further 23 parts of triethylamine were added, followed by 585 parts of water. The two phase reaction mixture was heated to 50°–55° C; and then allowed to separate. The lower, triethylamine hydrochloride, layer was removed and the upper organic was passed to stage (c).

Stage (c)

To the solution from stage (b) were added 350 parts of ethyl alcohol, 43 parts of water, and 655 parts of 30% w/w hydrochloric acid. The temperature rose to 47° C. The two-phase reaction mixture was agitated for 16 hours with cooling to 20° C and after settling, the lower aqueous layer was removed.

The upper solvent layer was distilled to remove the bulk of the untreated ethyl alcohol, and washed with sodium carbonate solution to remove traces of hydrochloric acid. The solution was then distilled to remove the remaining toluene leaving 564 parts of 2,3-dihydro-3,3-dimethyl-2-ethoxy benzofuran-5-yl-methane sulphonate - yield 87.5% on the technical benzoquinone used in Stage (a).

EXAMPLE 7

Alternative method for carrying out Stage (b) in Example 6 - Preparation of 2,3-dihydro-3,3-dimethyl-5-hydroxy-2-ethoxy-benzofuran 97 Parts of 2,3-dihydro-3,3-dimethyl-5-hydroxy-2-morpholinobenzofuran prepared as in Stage (a) of Example 6 were allowed to air-dry after filtration and were added to 513 parts of ethyl alcohol and 32.5 parts of water. To this were added 72 parts of concentrated sulphuric acid and the mixture was refluxed for 4 hours.

The reaction mixture was cooled and poured into 3200 parts of ice and water to give an oil which solidified on seeding with previously prepared product. This product was filtered off and air dried. Yield: 57.7 parts, purity by GLC 95%, equivalent to a molar yeild of 67.5%. Continuous ether extraction of the filtrate showed that a further 5.5% of product had remained in solution.

Preparation of 2,3-dihydro-3,3-dimethyl-2-ethoxy-benzofuran-5-yl methane sulphonate 8.32 parts of the above product were dissolved in 20 parts of toluene and 6 parts of triethylamine. To this were added 6.3 parts of methane sulphonyl chloride over 0.2 hours, the temperature being maintained at 40°–45° C. 15 parts of water were added with agitation, and after separation of the lower layer and evaporation to dryness, 11.7 parts of product were obtained, purity 91% by GLC, equivalent to a 98% molar yield.

EXAMPLE 8

The process of Example 1 was repeated using 196.2 parts of piperidine in place of the morpholine. The product was the corresponding piperidino enamine which was reacted with benzoquinone in toluene to give 2,3-dihydro-3,3-dimethyl-5-hydroxy-2-piperidinobenzofuran. This was converted to 2,3-dihydro-3,3-dimethyl-2-piperidino-benzofuran-5-yl methanesulphonate and then to 2,3-dihydro-3,3-dimethyl-2-ethoxy-benzofuran-5-yl methane sulphonate as in Example 5.

EXAMPLE 9

The process of Example 8 was repeated using 163.9 parts of pyrrolidine in place of the piperidine to give the pyrrolidino enamine and then 2,3-dihydro-3,3-dimethyl-5-hydroxy-2-pyrrolidinobenzofuran which was subsequently treated as in Example 5.

EXAMPLE 10

The process of Example 8 was repeated using 555.4 parts of di(2-ethyl-hexyl)amine in place of the piperidine to give the corresponding 2-ethyl-hexyl enamine and then 2,3-dihydro-3,3-dimethyl-5-hydroxy-2-di(2-ethyl-hexyl)amino-benzofuran which was subsequently treated as in Example 5.

EXAMPLE 11

Stage (c) of Example 6 was repeated using 244 parts of methanol in place of the ethanol to give 2,3-dihydro-3,3-dimethyl-2-methoxybenzofuran-5-yl methanesulphonate.

EXAMPLE 12

The process of Example 11 was repeated using 457 parts of propyl alcohol in place of the methanol to give 2,3-dihydro-3,3-dimethyl-2-propoxy-benzofuran-5-yl methanesulphonate.

EXAMPLE 13

The process of Example 12 was repeated using 776 parts of hexyl alcohol in place of the methanol to give 2,3-dihydro-3,3-dimethyl-2-hexyloxy-benzofuran-5-yl methanesulphonate.

I claim:

1. A process for preparing a compound of the formula:

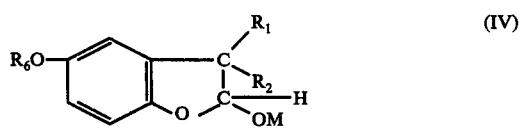

wherein $R_1$ and $R_2$ are the same or different and each is selected from the group consisting of hydrogen, alkyl of 1 to 6 carbon atoms and, together, alkylene of 2 to 5 carbon atoms chain; M is alkyl of 1 to 6 carbon atoms; and $R_6$ is selected from the group consisting of hydrogen and $R_5SO_2$— wherein $R_5$ is alkyl of 1 to 6 carbon atoms, which comprises:

Stage (a) reacting benzoquinone with an enamine of the formula:

$$R_1R_2C=CH-NR_3R_4 \quad (II)$$

wherein $R_1$ and $R_2$ are as defined above, $R_3$ is alkyl of 1 to 6 carbon atoms and $R_4$ is selected from the group consisting of alkyl of 1 to 6 carbon atoms and with $R_3$, together with the N atom, a heterocyclic ring selected from the group of morpholino, piperidino and pyrrolidino in the presence of a compound of the formula $R_1R_2CHCHO$, whereby there is produced a compound of the formula:

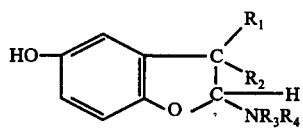
(I)

Stage (b) reacting a compound of formula:

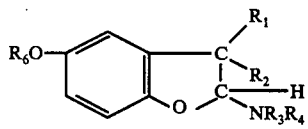
(V)

with an acid and a compound of the formula HOM (where M has the values given above), whereby there is produced a compound of formula IV.

2. A process as in claim 1 wherein Stage (b) is carried out in one stage using a mixture of the acid and the compound HOM.

3. A process as in claim 1 wherein the product compound of formula IV has $R_6$ as hydrogen and is reacted with a compound of formula $R_5SO_2Hal$ wherein Hal is hydrogen to give a compound of formula

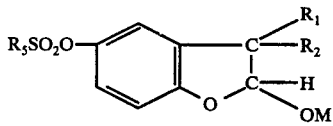

4. A process according to claim 1 wherein between Stages (a) and (b) the compound of formula (I) is reacted with a compound of the formula $R_5SO_2Hal$ wherein Hal is halogen to give a compound of formula (V) wherein $R_6$ is a group $R_5SO_2-$.

5. A process as in claim 1 wherein the compound of formula (IV) is 2,3-dihydro-3,3-dimethyl-2-ethoxy-benzofuran-5-yl methane sulphonate.

6. A process for preparing a compound of the formula

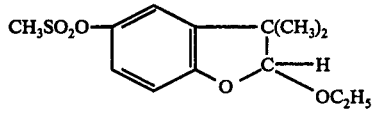

which comprises reacting p-benzoquinone with from 1 to 4% molar overall excess of the enamine

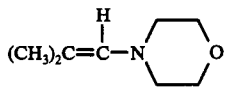

in the presence of from 10 to 200 molar percent of isobutyraldehyde based on the enamine in an aromatic hydrocarbon medium; reacting the reaction product with $CH_3SO_2Cl$ in the presence of an acid acceptor; and reacting the reaction product with a mixture of ethyl alcohol and a mineral acid selected from the group consisting of sulphuric acid, hydrochloric acid and phosphoric acid.

7. A process as claimed in claim 1 wherein the compound of formula II is prepared by reacting a compound of the formula $HNR_3R_4$ with an excess of the compound $R_1R_2CHCHO$ to give a reaction mixture containing the compounds of formula II and $R_1R_2CHCHO$; and reacting said reaction mixture with benzoquinone.

8. A process as in claim 1 wherein in the reaction between the benzoquinone and the compound of formula II, the compound of formula II is present at substantially all times in more than the stoichiometric amount required to react with the benzoquinone present in the reaction mixture.

9. A process as in claim 1 wherein water is removed from the reaction mixture containing the compound of formula (II) before it is reacted with benzoquinone.

* * * * *